(12) United States Patent
Zuk et al.

(10) Patent No.: US 8,501,496 B2
(45) Date of Patent: Aug. 6, 2013

(54) IMMUNOASSAY CUVETTES

(71) Applicant: Access Medical Systems, Ltd., Palo Alto, CA (US)

(72) Inventors: Robert F. Zuk, Menlo Park, CA (US); Hong Tan, San Jose, CA (US)

(73) Assignee: Access Medical Systems, Ltd., Palo Alto, CA (US)

( * ) Notice: Subject to any disclaimer, the term of this patent is extended or adjusted under 35 U.S.C. 154(b) by 0 days.

(21) Appl. No.: 13/654,299

(22) Filed: Oct. 17, 2012

(65) Prior Publication Data
US 2013/0040378 A1 Feb. 14, 2013

Related U.S. Application Data

(62) Division of application No. 12/369,564, filed on Feb. 11, 2009, now Pat. No. 8,304,255.

(60) Provisional application No. 61/027,749, filed on Feb. 11, 2008.

(51) Int. Cl.
*G01N 33/543* (2006.01)

(52) U.S. Cl.
USPC ............ 436/518; 422/401; 422/402; 422/408

(58) Field of Classification Search
USPC .......................... 422/401, 402, 408; 436/518
See application file for complete search history.

(56) References Cited

U.S. PATENT DOCUMENTS

| | | |
|---|---|---|
| 4,829,010 A | 5/1989 | Chang |
| 5,432,099 A | 7/1995 | Ekins |
| 5,578,832 A | 11/1996 | Trulson et al. |
| 6,140,044 A | 10/2000 | Besemer et al. |

*Primary Examiner* — Monique Cole
(74) *Attorney, Agent, or Firm* — Perkins Coie LLP.; Viola T. Kung

(57) ABSTRACT

The present invention is directed immunoassay cuvettes that comprise diffusely bound and non-diffusely bound reagents for carrying out an immunoassay. The reaction and detection are carried out in the immunoassay cuvette. The immunoassay cuvette comprises a transparent front wall, a back wall, side walls, a bottom, and a top opening. The back wall of the cuvette has a substantially planar surface made of a non-porous material and comprises a capture zone having reagents non-diffusedly bound and a signal reagent zone having reagents diffusedly bound.

9 Claims, 11 Drawing Sheets

IMMUNOASSAY CUVETTES

This application is a divisional of U.S. application Ser. No. 12/369,564, filed Feb. 11, 2009, which claims the benefit of U.S. Provisional Application No. 61/027,749, filed Feb. 11, 2008. The above applications are incorporated herein by reference in their entirety.

FIELD OF THE INVENTION

The present invention relates to an immunoassay cuvette that comprises diffusely bound and non-diffusely bound reagents for carrying out an immunoassay. The reaction and detection are carried out in the immunoassay cuvette.

BACKGROUND OF THE INVENTION

A bench top immunoassay analyzer is considered to have medium sample throughput capability falling between POC (point of care) and high volume analyzers. Where POC instruments measure 1 or 2 samples at a time and high volume systems are capable of handling hundreds to thousands of samples, bench top analyzers with medium throughput can accommodate somewhere around the range of ten to one hundred samples. The term "bench top" used to describe these medium throughput analyzers indicates the instruments are intended to be small enough to be placed in small to mid sized clinics on laboratory benches.

One challenge to the design of a bench top analyzer is that some clinical situations demand multi-analyte capability where several markers are measured in the same sample. Multi-analyte capability can offer the user more rapid result turn around time and greater convenience with lower cost compared to running individual assays for each marker in the panel. A bench top analyzer should be capable of offering a full menu of immunoassays (over 50 assays) and many of these assays have different protocols, assay times and reagents, all of which demand that the instrument system including the consumables (disposable reagents and immunoassay devices) have the flexibility to accommodate these differing assay requirements. Another challenge is that in clinical labs, bench space is at a premium and the "foot print" of an instrument is a major consideration.

Clinical immunoassay analyzers offer a full menu of assays; they need to have all or many of the assay reagents in the menu residing in the instrument in order to be available when test panels are ordered. The storage of multiple reagent vials adds to the space and complexity of the instrument system. The fluid handling subsystem must be capable of withdrawing an aliquot from the reagent vial and dispense it into a test device along with sample. Often to achieve long term stability of the assay reagents, the storage chamber is be refrigerated. FIG. 1 shows a typical bench top analyzer manufactured by Adaltis with the reagent vials, cuvette tray and the major subsystems within the instrument. A major portion of the instrument illustrated in FIG. 1 is dedicated to storage of reagents and calibrators necessary to offer a full menu assays.

Since consumables (reagents and immunoassay devices) are central to the design of an immunoassay instrument system, there is a need for unitized consumables that keep all the essential reagents in one unit and in a dry format. The unitized consumables improve the reagent stability, reduce the complexity and overall size of a bench top analyzer, and add to user convenience.

SUMMARY OF INVENTION

The present invention is directed to immunoassay cuvettes comprising a transparent front wall, a back wall, side walls, a bottom, and a top opening.

In one embodiment, the immunoassay cuvette is suitable for a one-step immunoassay either in a competitive format or a sandwich format. In this embodiment, the back wall of the cuvette has a substantially planar surface made of a non-porous material and comprises a capture zone and a signal reagent zone. The capture zone comprises one or more spots each non-diffusely bound with a first member of a binding pair. The signal reagent zone having one or more spots diffusely bound with a signal reagent comprising the first member or a second member of the binding pair.

In another embodiment, the immunoassay cuvette is suitable for a two-step sequential binding immunoassay either in a competitive format or a sandwich format, when the analyte is an antigen. In this embodiment, the back wall of the cuvette has a substantially planar surface made of a non-porous material and comprises a capture zone, a binding reagent zone, and a signal reagent zone. The capture zone comprises one or more spots non-diffusely bound with a first antibody against a defined antigen. The binding reagent zone comprises one or more spots diffusely bound with a binding reagent comprising (a) the defined antigen or (b) a second antibody against the defined antigen. The signal reagent zone has one or more spots each diffusely bound with a signal reagent comprising a conjugate of a signal generating molecule and a binding molecule that binds to the binding reagent but does not bind to the first antibody. The signal reagent zone is located above the binding reagent zone and the capture zone.

In another embodiment, the immunoassay cuvette is suitable for a two-step sequential binding immunoassay either in a competitive format or a sandwich format, when the analyte is an antibody. In this embodiment, the back wall has a substantially planar surface made of a non-porous material comprising a capture zone, and a signal reagent zone. The capture zone comprises one or more spots each non-diffusely bound with a defined antigen. The signal reagent zone having one or more spots diffusely bound with a signal reagent comprising an antibody against a human immunoglobulin such as IgG or IgM, wherein the signal reagent zone is located above the capture zone.

DETAILED DESCRIPTION OF THE INVENTION

Definitions

Figure 1:
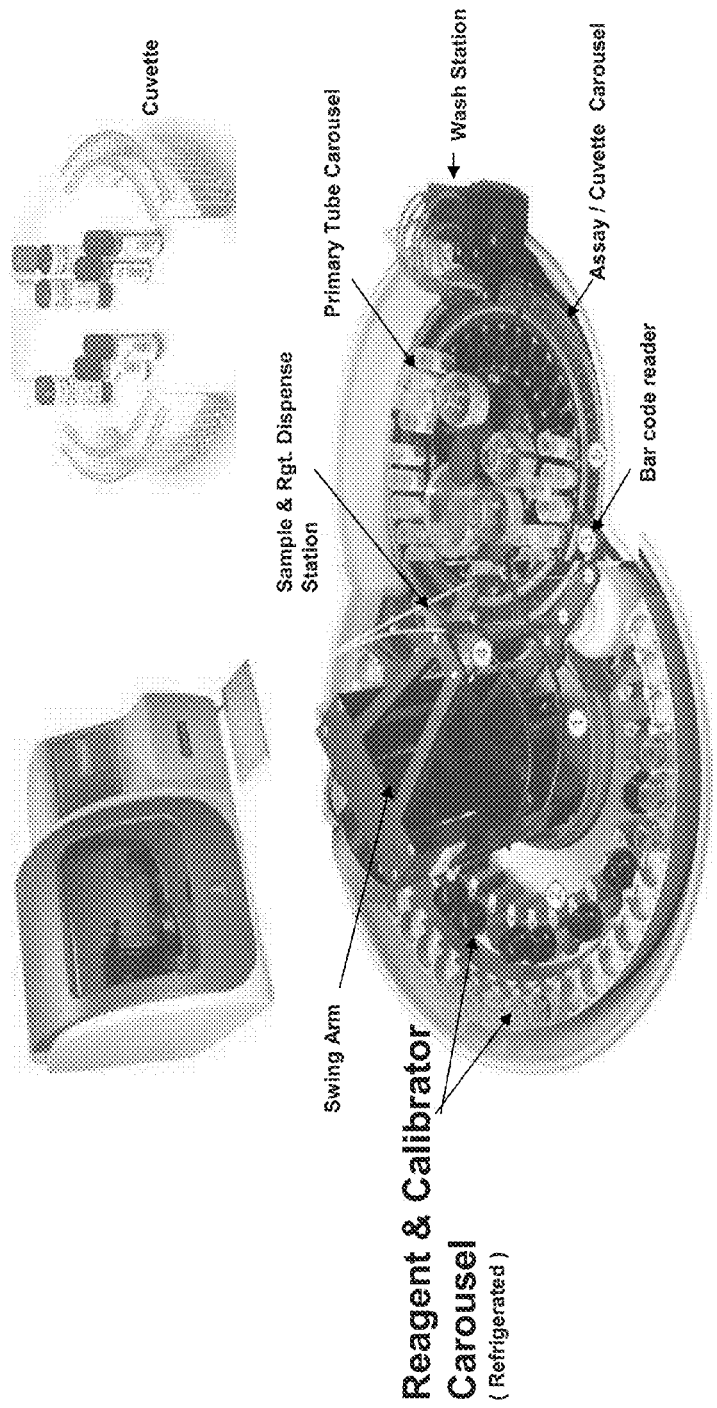
FIG. 1 depicts a prior art bench top analyzer.

A binding pair, as used herein, refers to two molecules that are attracted to each other and specifically bind to each other. Examples of binding pairs include, but not limited to, an antigen and an antibody against the antigen, a ligand and its receptor, complementary strands of nucleic acids, biotin and avidin, biotin and streptavidin.

Diffusively bound, as used herein, refers to reagents deposited in a dry format on a solid phase. When a liquid sample is added to the solid phase, such reagents become free to diffuse in the liquid medium. Examples of diffusively bound reagents in this application include reagents in the signal reagent zone and binding reagent zone.

Immobilized, as used herein, refers to reagents being fixed to a solid surface. When a reagent is immobilized to a solid surface, it is either diffusely bound or non-diffusely bound to the surface.

Non-diffusively bound, as used herein, refers to reagents immobilized to a solid phase and are not free to diffuse in a liquid medium. Examples of non-diffusively bound reagents in this application are reagents in the capture zone.

A signal generating molecule refers to a molecule that can generate signals for detection. For example, a signal generating molecule is a fluorescent dye, a chemiluminescent dye, or an enzyme (e.g. alkaline phosphatase or β-galactosidase) that can react on a substrate to generate signals.

A non-porous material, as used herein, refers to a material that has less than 20%, preferably less than 10%, preferably less than 5%, mostly preferably less than 1% of its volume occupied with void spaces. A non-porous material includes, but not limited to plastics such as polymethylmethacrylate, polystyrene, polycarbonate, glass, quartz, or combination thereof.

The present invention provides various formats of immunoassay cuvettes suitable for a bench top clinical immunoassay analyzer. The immunoassay cuvettes are unitized consumables that contain all the essential reagents for immunoassays in a dry format. Unlike prior art bench top analyzer, which reagents and calibrators have to be stored refrigerated within the analyzer, the immunoassay cuvettes have excellent long term stability and they do not have to be stored within the instrument at refrigerated temperature. The immunoassay cuvettes keep incompatible reagents separated, for example, in capture zone and reagent zone until the assay is started.

The immunoassay cuvette of the present invention is a reaction chamber designed for one or more immunoassay reactions, which provide a signal for detecting analytes. The immunoassay cuvette comprises a transparent front wall, a back wall, side walls, a bottom, and a top opening. The back wall has a substantially planar surface made of a non-porous material, which the essential reagents are immobilized on.

One-Step Binding Reaction

This format has a capture zone (non-diffusely bound) and reagent zone (diffusively bound), which work for one binding step assays, i.e. no need for sequential binding. The prime advantage of sequential binding is that it can amplify signals and improve sensitivity; however, not every assay requires high sensitivity or needs amplification. For the one step assays, the diffusively bound reagent is labeled with a signal generating molecule such as a fluorescent dye. Another feature of this format is that it keeps incompatible reagents separated in capture and reagents zones until the assay is started. This is mandatory for competitive assays.

The immunoassay cuvette for a one-step binding reaction can be designed in a competitive assay format or in a sandwich assay format. The back wall of the immunoassay cuvette comprises a capture zone and a signal reagent zone. The capture zone comprises one or more spots each non-diffusely bound with a first member of a binding pair, and the signal reagent zone having one or more spots diffusely bound with a signal reagent comprising the first member or a second member of the binding pair. In this embodiment, when the signal reagent comprises the first member of the binding pair, it is a sandwich assay. When the signal reagent comprises the second member of the binding pair, it is a competitive assay.

In one embodiment, the immunoassay cuvette has a capture zone that comprises 1 to 20 spots, preferably 1-8 spots, each non-diffusely bound with a first member of a binding pair, such as an antibody. In a multianalyte format, spots can be dedicated, for example, to members of a binding pair, to serve as a procedural control. A procedure control in this case can be an antigen/antibody pair that does not occur in human samples. A binding reaction can then be constructed to give a consistent fluorescent signal from sample to sample. The procedural control then acts to monitor whether the instrument performed the assay correctly, if reagents remained stable during storage, or if the correct cuvette was used. Examples of antigen/antibody pairs suitable of procedural controls would be fluorescein/anti-fluorescein and dinitrophenol/anti-dinitrophenol. One member of the procedural control binding pair is non-diffusively bound in a spot in the capture zone and the second member, labeled with a fluorescent tag, can be diffusively bound in either the binding reagent zone or signal reagent zone. In a preferred embodiment, the signal reagent zone has only one spot.

Sandwich Assay Format

Figure 2:
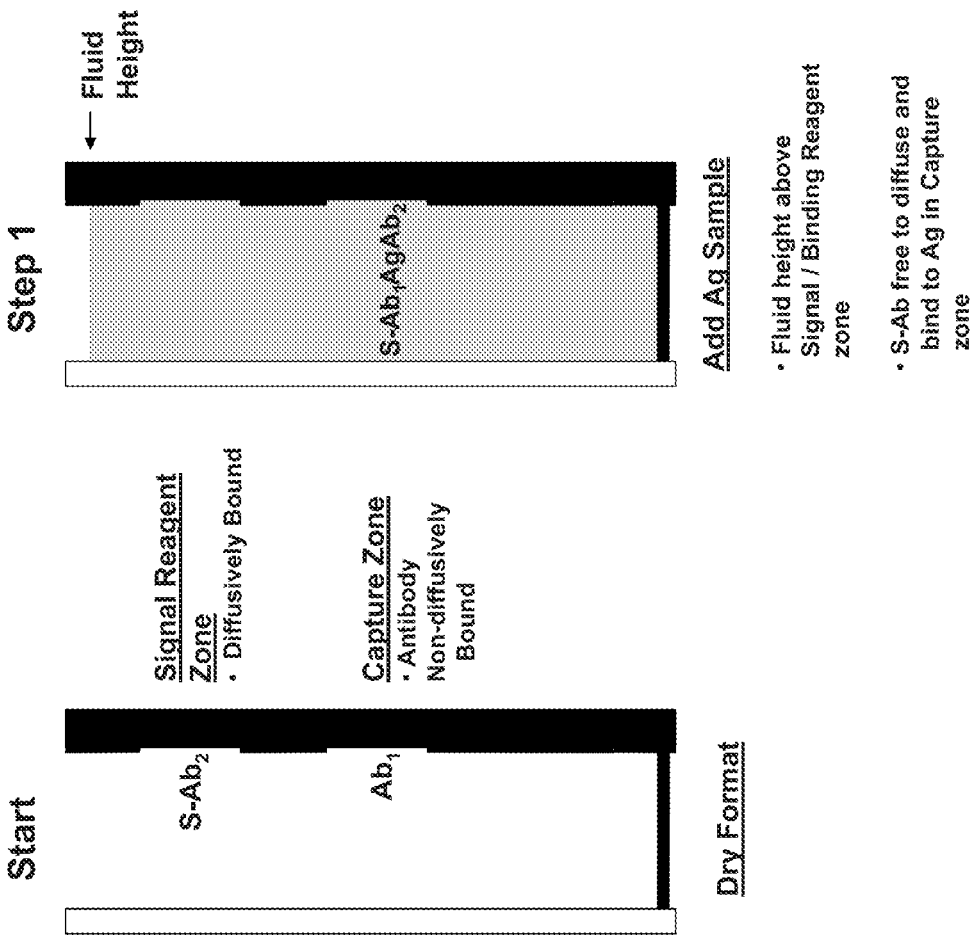
FIG. 2 shows a one-step binding reaction in a sandwich assay, where the analyte is an antigen.

FIG. 2 illustrates the immunoassay cuvette designed for a sandwich assay where the analyte is an antigen. In the capture zone, the spot is non-diffusely bound with a first antibody against the antigen. In the signal reagent zone, the spot is diffusely bound with a signal reagent comprising a second antibody against the antigen. The first and the second antibody can be identical or different. When the first and the second antibody are different, they can be monoclonal antibodies against different epitopes, or they can be different polyclonal antibodies, or they can be monoclonal antibody and polyclonal antibody. In FIG. 2, the antibody is label with a signal generating molecule such as a fluorescent dye (S-Ab). When the antigen sample is added to the cuvette, the fluid height should be above both the capture zone and the signal reagent zone. The S-Ab is free to diffuse and binds to antigen capture by the antibody in the capture zone and provides a signal.

Figure 3:
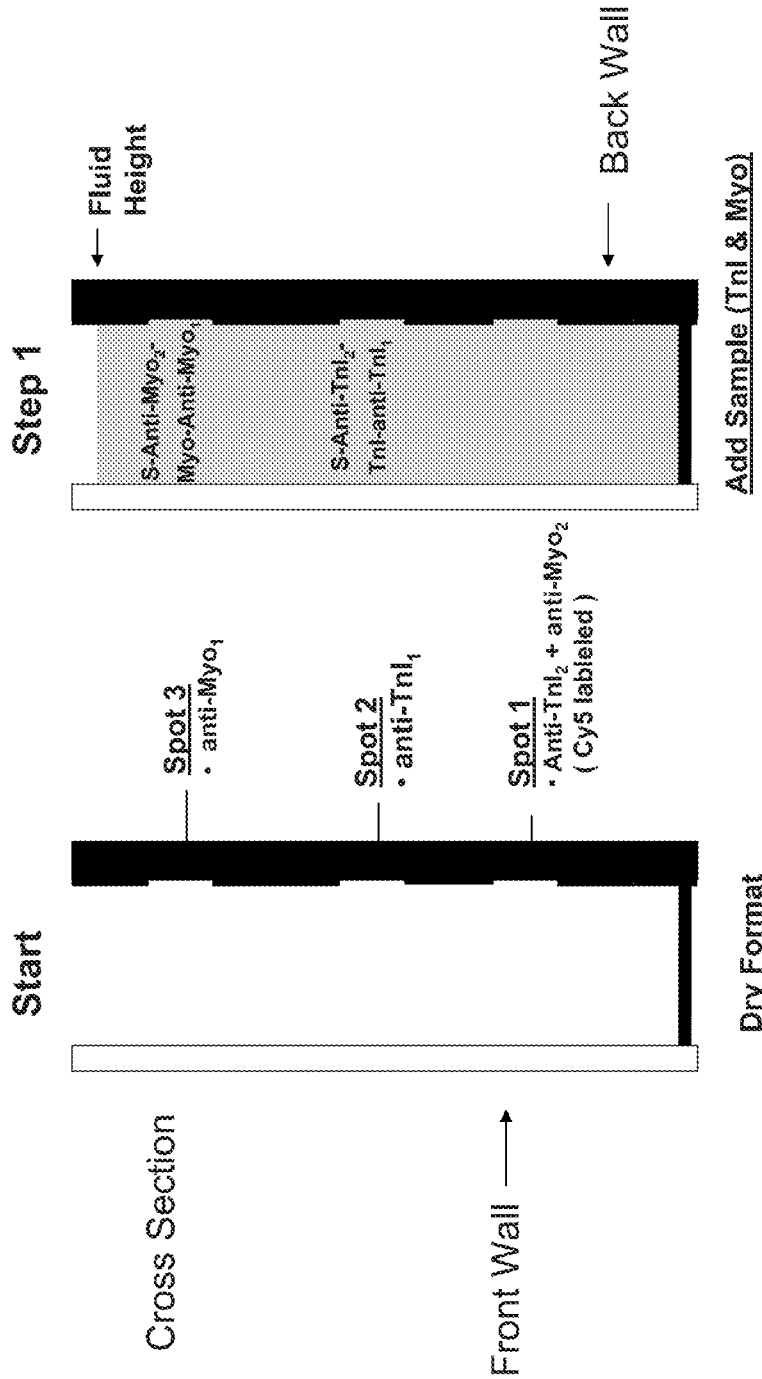
FIG. 3 shows a one-step binding reaction in a sandwich assay, where the analytes are multiple antigens.

FIG. 3 and Example 2 illustrate the immunoassay cuvette designed for sandwich assays for multiple antigen analytes. In the capture zone, spot 1 is non-diffusely bound with a first antibody against Antigen 1, myoglobin. Spot 2 is non-diffusely bound with a first antibody against Antigen 2, troponin I. In the signal reagent zone, spot 1 is diffusely bound with a signal reagent comprising a second antibody against Antigen 1 and a second antibody against Antigen 2. The antibodies are labeled with a signal generating molecule such as a fluorescent dye (S-Ab). When the antigen sample is added to the cuvette, the fluid height is designed to be above both the capture zone and the signal reagent zone. The signal labeled-antibodies are free to diffuse and bind to Antigen 1 and Antigen 2 captured by its respective antibody in the capture zone and provide a signal in spot 2 and spot 3.

Competitive Assay Format

In a one step binding, competitive assay format for an antigen analyte, the capture zone has the antigen non-diffusedly immobilized. The signal reagent zone is diffused bound with the antibody labeled with a signal generating molecule. When the antigen sample is added to the cuvette, the fluid height should be above both the capture zone and the signal reagent zone. The signal labeled-antibody is free to diffuse and binds either to the antigen in the sample or the antigen in the capture zone In a one step binding, competitive assay format for an antigen analyte, the capture zone has the antibody non-diffusedly immobilized. The signal reagent zone is diffusedly bound with the antigen labeled with a signal generating molecule. When the antigen sample is added to the cuvette, the fluid height should be above both the capture zone and the signal reagent zone. The signal labeled-antigen is free to diffuse and compete with the antigen in sample for binding to the antibody in the capture zone.

Figure 4:
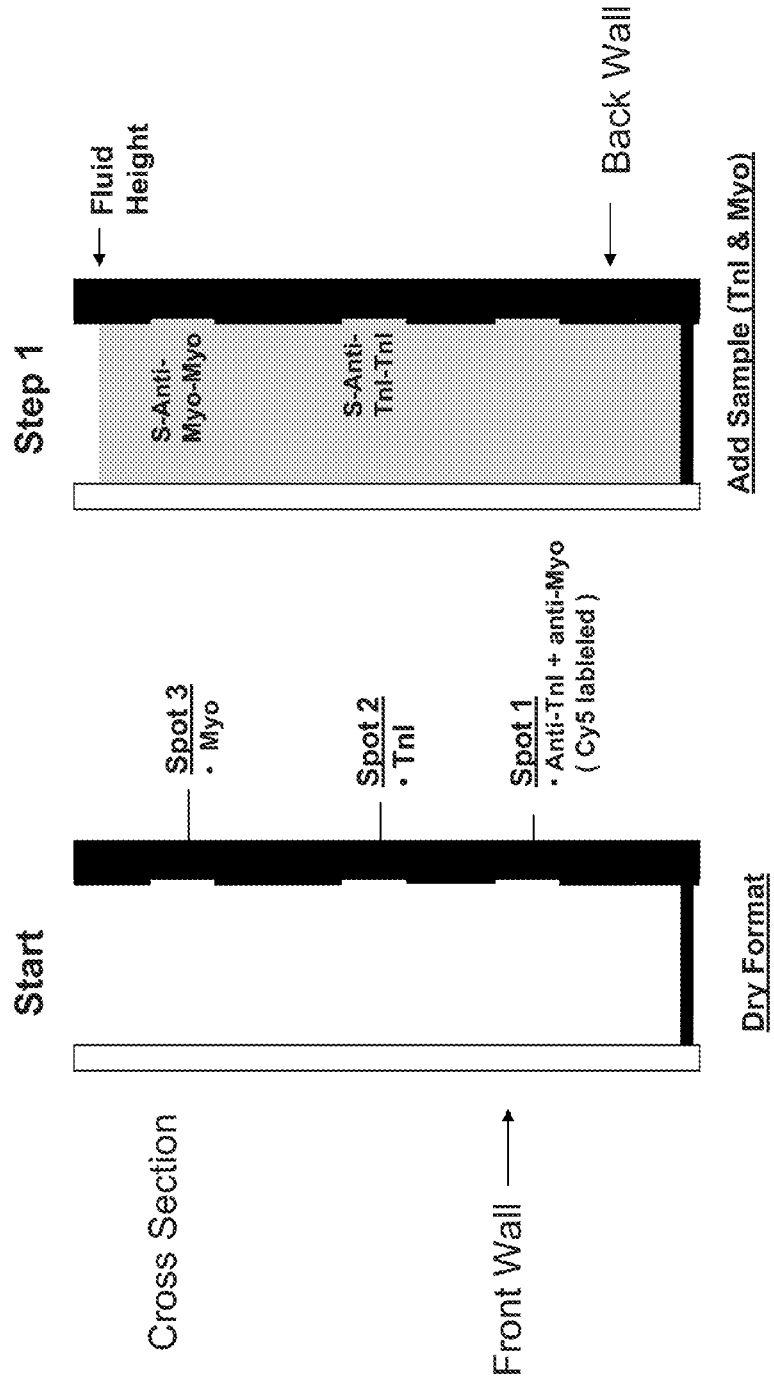
FIG. 4 shows a one-step binding reaction in a competition assay, where the analytes are multiple antigens.

FIG. 4 and Example 3 illustrate the immunoassay cuvette designed for competitive assays for multiple antigen analytes. In the capture zone, spot 3 is non-diffusely bound with Antigen 1, e.g., myoglobin. Spot 2 is non-diffusely bound Antigen 2, e.g., troponin I. In the signal reagent zone, spot 1 is diffusely bound with a signal reagent comprising an antibody against Antigen 1 and an antibody against Antigen 2. The antibodies are labeled with a signal generating molecule such as a fluorescent dye (S-Ab). When the antigen sample is added to the cuvette, the fluid height should be above both the capture zone and the signal reagent zone. The signal labeled-antibodies are free to diffuse and bind either to the Antigens 1 and 2 in the sample or the Antigens 1 (spot 3) and 2 (Spot 2) in the capture zone.

Two-Step Sequential Binding Reaction

Sequential format are suitable for assays that need high sensitivity. The sequential format offers a two-step sequential binding protocol, where the second step has a signal amplification reagent that binds to complexes in the capture zone. The reason why a two step binding protocol is needed is that if a signal reagent is present in the first binding step, it will interfere with the formation of the immune complex in the capture zone. The immune complex must be formed first before the signal reagent binds; therefore a sequential protocol is required. The sequential format is suitable for both sandwich and competitive binding assays in single and multianalyte modes.

Antigen Analyte

In this embodiment, the immunoassay cuvette is designed for a two-step binding reaction either in a competitive assay format or in a sandwich assay format. The back wall of the immunoassay cuvette comprises a capture zone, a binding reagent zone, and a signal reagent zone.

The capture zone comprises one or more spots non-diffusely bound with a first antibody against a defined antigen. The binding reagent zone comprises one or more spots diffusely bound with a binding reagent comprising (a) the defined antigen (for a competitive assay format) or (b) a second antibody against the defined antigen (for a sandwich assay format). (a) or (b) can be labeled with a first member of a binding pair such as biotin/streptavidin.

The signal reagent zone has one or more spots diffusely bound with a signal reagent comprising a conjugate of a signal generating molecule and a binding molecule that binds to the binding reagent but does not bind to the first antibody. The binding molecule either binds to the second antibody or binds to the first member of the binding pair. The signal reagent zone is located above the binding reagent zone and the capture zone.

Figure 5:
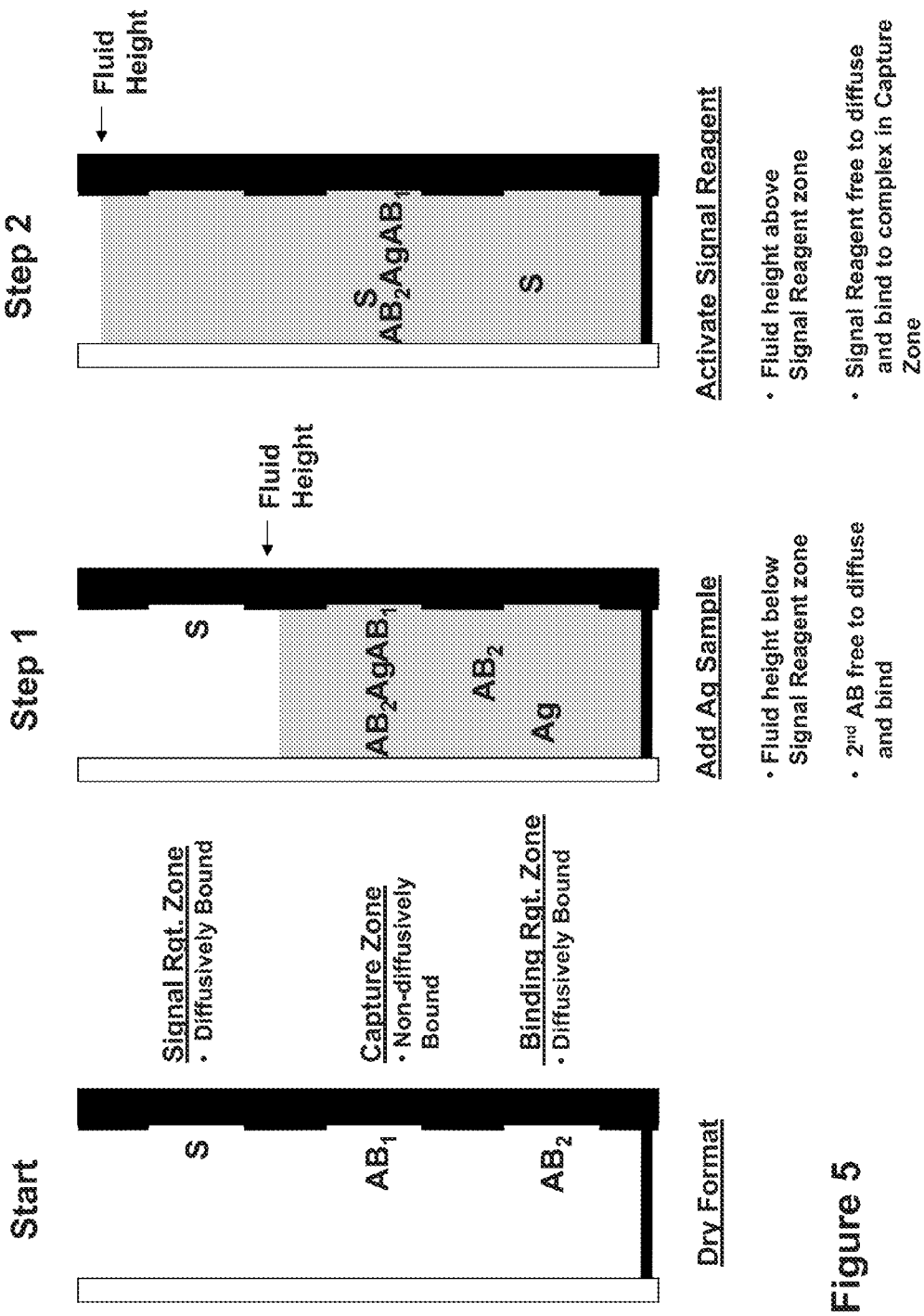
FIG. 5 shows a two-step sequential binding reaction in a sandwich assay, where the analyte is an antigen.

FIG. 5 illustrates the immunoassay cuvette designed for a two-step, sequential binding sandwich assay, where the analyte is an antigen. The capture zone comprises one or more spots non-diffusely bound with a first antibody against a defined antigen. The binding reagent zone comprises one or more spots diffusely bound with a binding reagent comprising a second antibody against the defined antigen. The signal reagent zone has one or more spots diffusely bound with a signal reagent comprising a conjugate of a signal generating molecule and a binding molecule that binds to the binding reagent (e.g., the second antibody) but does not bind to the first antibody. The signal reagent zone is located above the binding reagent zone and the capture zone. When an antigen sample is added, the fluid height is below the signal reagent zone, and the second antibody is free to diffuse and bind to the antigen captured in the capture zone. After washing to remove the unbound materials, a buffer is added to above the height of the signal reagent zone. The signal reagent is dissolved in the buffer and freely to diffuse and bind to complex in the capture zone.

FIG. 5 illustrates the fluid management with the Unitized Consumable to conduct assays with sequential reactions. Diffusively bound and non-diffusively bound reagents are brought into reaction when there respective zones are hydrated by addition of a diluent reagent to the cuvette. Since the zones are positioned at specified heights on the vertical wall, sequential reactions can be performed by increasing the volume of diluent reagent thereby hydrating zones at higher locations on the cuvette wall. FIG. 5 is an example of a sandwich immunoassay with one antibody non-diffusively bound in the capture zone and the second antibody diffusively bound in the reagent binding zone. Addition of a diluent reagent containing sample antigen initiates the first binding reaction. The volume of the diluent reagent is such that the fluid height is below the Signal Reagent Zone. Since most sandwich immunoassays are heterogeneous, the immunoassay cuvette is flexible for incubation times and number of wash cycle as long as the fluid height is maintained below the Signal Reagent Zone. At the completion of the first binding reaction, the second reaction is started by adding a volume of diluent reagent so that the fluid height is higher than the signal reagent zone, which in this case hydrates a fluorescent binding reagent that can bind to immune complexes in the capture zone. After incubation period and wash cycle, fluorescence in the capture zone is measured.

Three-Step Sequential Binding Reaction, Antigen Analyte

In a three-step assay, the immunoassay cuvette's design is similar to that of the above-described for a two-step assay, except the binding reagent zone is located above the capture zone.

Figure 6:
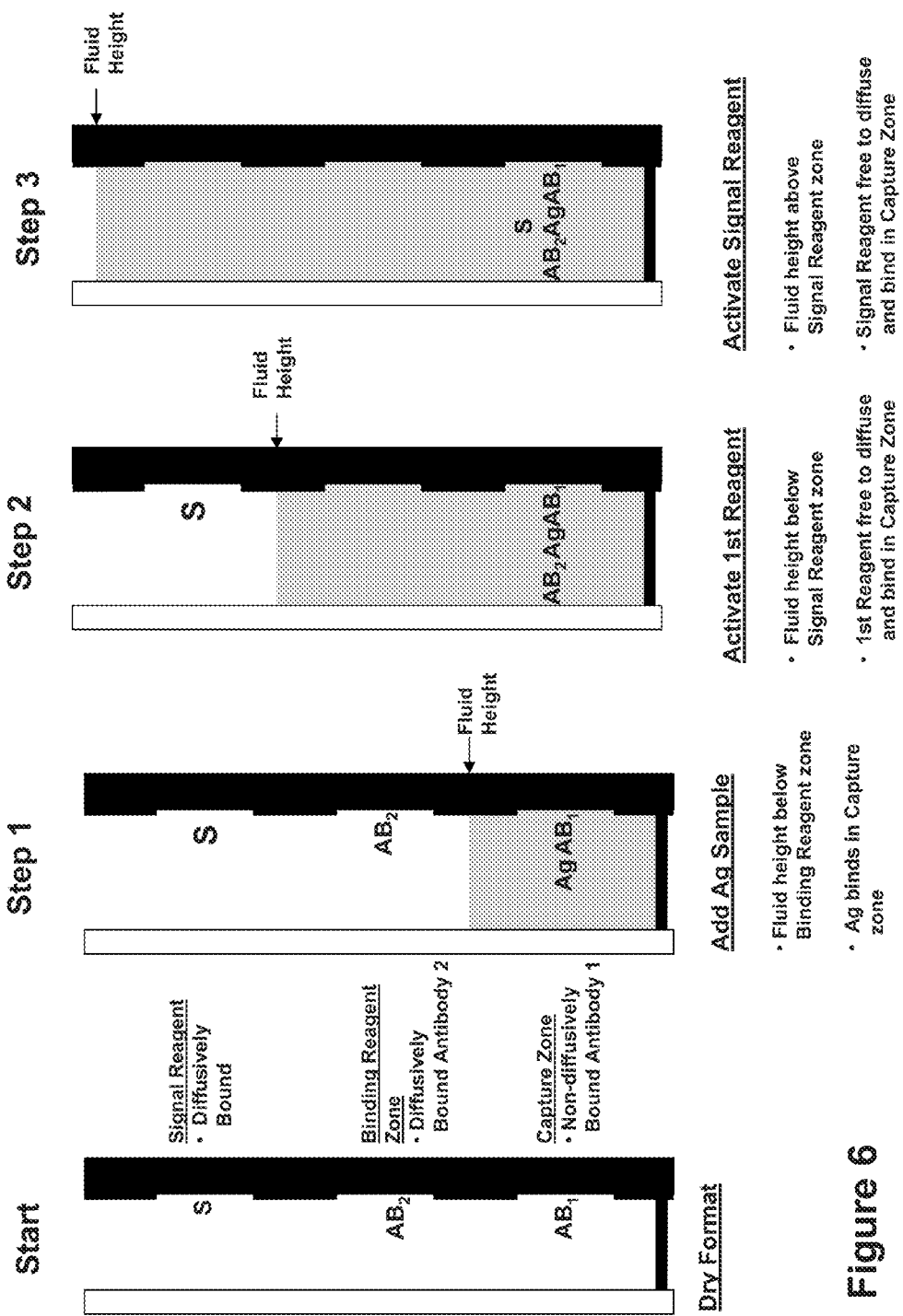
FIG. 6 shows a three-step sequential binding reaction in a sandwich assay, where the analyte is an antigen.

FIG. 6 illustrates the immunoassay cuvette designed for a three-step, sequential binding sandwich assay, where the analyte is an antigen. The capture zone comprises one or more spots non-diffusely bound with a first antibody against a defined antigen. The binding reagent zone comprises one or more spots diffusely bound with a binding reagent comprising a second antibody against the defined antigen. The signal reagent zone has one or more spots diffusely bound with a signal reagent comprising a conjugate of a signal generating molecule and a binding molecule that binds to the binding reagent (e.g., the second antibody) but does not bind to the first antibody. The signal reagent zone is located above the binding reagent zone, and the binding reagent zone is located above the capture zone. When an antigen sample is added, the fluid height is below the binding reagent zone, and the antigen binds to the antibody in capture zone. After washing, fluid is added to below the signal reagent zone to hydrate the binding reagent, which is freely diffused and binds to the complex in the capture zone. After washing, fluid is added to hydrate the signal reagent, which is freely diffused and binds to the complex in the capture zone.

Two-Step Sequential Binding Reaction, Antibody Analyte, Sandwich Format

Another format of an immunoassay cuvette is designed for a sandwich assay where the analyte is an antibody, e.g., a serological assay for an antibody against hepatitis surface antigen such as hepatitis B or hepatitis C antigen. In this format, the capture zone comprises one or more spots each non-diffusely bound with a defined antigen. The signal reagent zone comprises one or more spots each diffusely bound with a signal reagent comprising an antibody against a human immunoglobulin (IgG or IgM), such as mouse anti-human IgG, wherein the signal reagent zone is located above the capture zone. In the signal reagent zone, the anti-immunoglobulin antibody is labeled with a signal generating molecule (such as fluorescent dye, enzyme, etc.) and there is no further amplification of the signal.

Alternatively, if the amplification of the signal is desired, a further signal reagent zone 2 above the first signal zone is provided. The anti-immunoglobulin antibody in the first signal reagent zone is labeled with a first member of a binding pair such as biotin/streptavidin, and the second signal zone comprises a conjugate of a signal generating molecule and a second member of the binding pair.

Manufacturing

Development of diffusively bound reagents on vertical walls of cuvette reaction chambers with smooth, non-porous surfaces requires the combination of several features. The reagents must be in a dry format and adhere firmly enough to the surface during manufacture, shipment and manipulation by users, until at the point of application. At a defined point in the assay protocol when the zone containing the diffusively bound reagent is immersed in a diluent, the reagent must rapidly solubilize, be free to diffuse in the liquid phase, and provide its intended biological or chemical activity. Stabilization of protein reagents, particularly antibodies, in a dry format, often requires additives to the protein formulation. Monomeric sugars, polysaccharides, and polyols are typical stabilizing additives. Selection of specific stabilizers in general is dependent on the particular assay format and drying method utilized. For example, a reagent containing sucrose at concentration ranging around 5-15% is sufficient to provide long term stability of the protein activity in a dry state, to adhere to a vertical wall of cuvettes and to solubilize rapidly in about 1 minute.

Although diffusively bound reagents are commonly applied in lateral flow test devices, such reagents are not suitable for application to non-porous vertical walls. Lateral flow devices introduce fluid by capillary action; reagent formulations are optimized to rapidly solubilize, in a matter of seconds, without perturbing the capillary flow. Adherence to the matrix is not an issue since lateral flow devices are constructed with membranes or fibrous materials that provide ample porosity and surface area to entrap the dried reagent. Conversely, formulations that are suitable for the vertical wall of the Unitized Consumable are not suitable for lateral flow device since they will not solubilize rapidly enough and will disrupt the uniformity of the capillary flow.

Methods to immobilize reagents to the solid phase are common in immunochemistry and involve formation of covalent, hydrophobic or electrostatic bonds between the solid phase and reagent. Non-diffusively bound reagents can be absorbed or covalently bound to the solid surface. Although the same adsorption method is used for immobilizing diffusively bound reagents, a large excess of carrier protein is present on the spotting reagent formulation to competitively inhibit adsorption of the specific reagent to the surface. Immobilization of non-diffusely bound and diffusely bound reagents on the back wall of an immunoassay cuvette is illustrated in Examples 2-5 in details.

Advantages of Immunoassay Cuvettes

The immunoassay cuvette is formatted to contain all of the reagents necessary to perform immunoassays for one or multiple biomarkers in a single sample using a common reaction chamber. Only addition of sample and a common diluent reagent are necessary to perform an assay. Because the assay reagents are contained within a cuvette, the reagent storage and dispensing are eliminated from the bench-top analyzer (see FIG. 1), thus reducing the overall size of the analyzer.

Protein arrays are often glass slide based and positioned on a horizontal plane within an instrument, which demands that a more complex closed fluid system be implemented with connectors, tubing, valves etc. The immunoassay cuvette of the present invention has a single opening at the top of the device; the opening is large enough for the insertion needles for dispensing or aspiration of reagents. In general, only two fluid management stations are required with the immunoassay cuvette, i.e., a sample/diluent buffer dispense station and an aspiration wash station. The sample/buffer dispense station can deliver fluids of specific volume to rehydrate reagent zones of a specific height.

Figure 7:
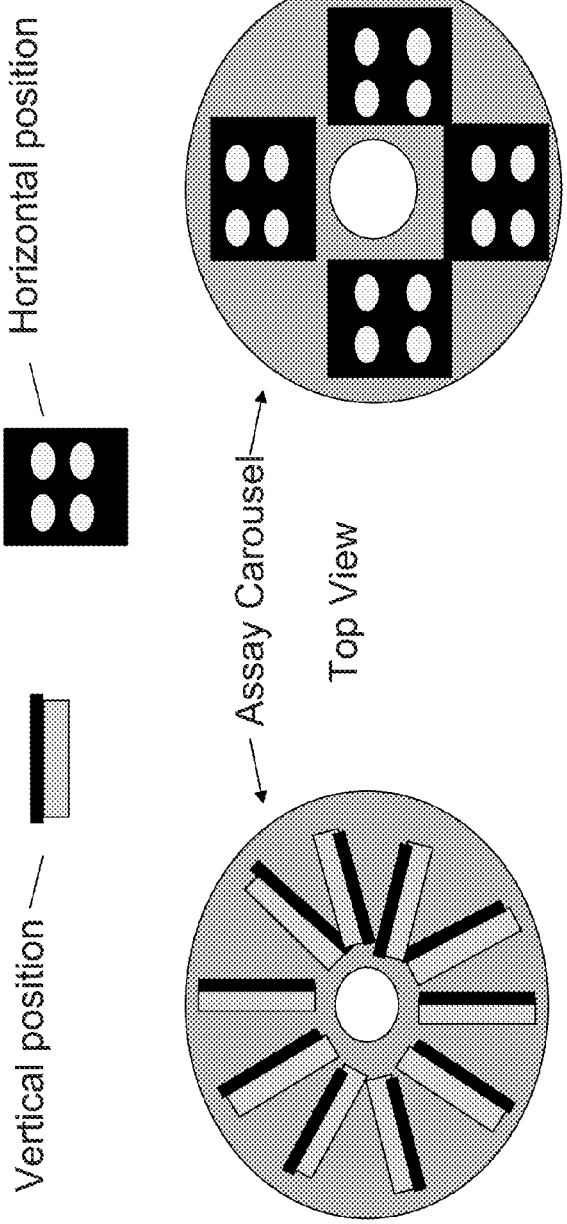
FIG. 7 shows vertical positioning of immunoassay cuvettes.

FIG. 7 shows a diagram of the immunoassay cuvette placed on a carousel, which illustrates another advantage of positioning the antibody capture zones in a vertical plane. In an analytical system designed to process multiple samples, there must be a subsystem to hold samples and consumables. This sample/consumable holding subsystem contributes to the sample capacity and foot print of the instrument system. These sample/consumable subsystems are often part of the mechanism to transfer the sample/consumables to different stations within the instrument to perform the assays. Carousels are used for radial motion and linked rail mechanisms are used for linear motion. For bench top systems, there is a compromise between the maximum sample capacity and the minimum foot print.

The immunoassay cuvette preferably has a unique aspect ratio between its height, width and thickness dimensions, such that positioning the reagent zones on the vertical walls can be a more efficient use of space, as depicted in FIG. 7. This feature of the immunoassay cuvette maximizes the sample capacity while minimizing the instrument foot print. Aspect ratio is defined as the ratio of height to the smallest dimension of either width or thickness. Aspect ratios around or greater than 3 to 1 are necessary to take advantage of space saving by positioning reagent zones on the walls of the cuvette. As used herein, height of a cuvette refers to the distance between the bottom of the cuvette and the top opening. Thickness of a cuvette refers to the distance between the front wall and the back wall. Width of a cuvette refers to the distance between the sidewalls.

The aspect ratio of the immunoassay cuvette facilitates the fluid removal (e.g., by aspiration) during the wash cycles of the assay. Wash cycles employing aspiration can be problematic for solid phase immunoassays with small capture zones, particularly arrays. The problem relates to the fact that the aspiration needle has to be brought into proximity of the capture zone in order to effect efficient fluid removal. At the end of the fluid removal, air flows into the needle at high rates since the aspiration is based on negative pressure. The air flow can cause the capture zone to dry out and inactive any binding reagent in the capture zone. Antibodies are especially prone to denaturation upon this type of drying. In situations where the aspiration needle is around 1 mm in diameter and the capture zone is a comparable dimension or smaller, a significant proportion of the binding reagent can be inactivated which results in poor reproducibility and other performance problems with the assay. Although ELISA assays with microplates are commonly carried out with plate washers using aspiration, some inactivation undoubtedly occurs, however, the effect is not noticeable due to the relatively large surface area of the microwell (6 mm diameter at bottom and about 5 mm high side walls.)

Figure 8:
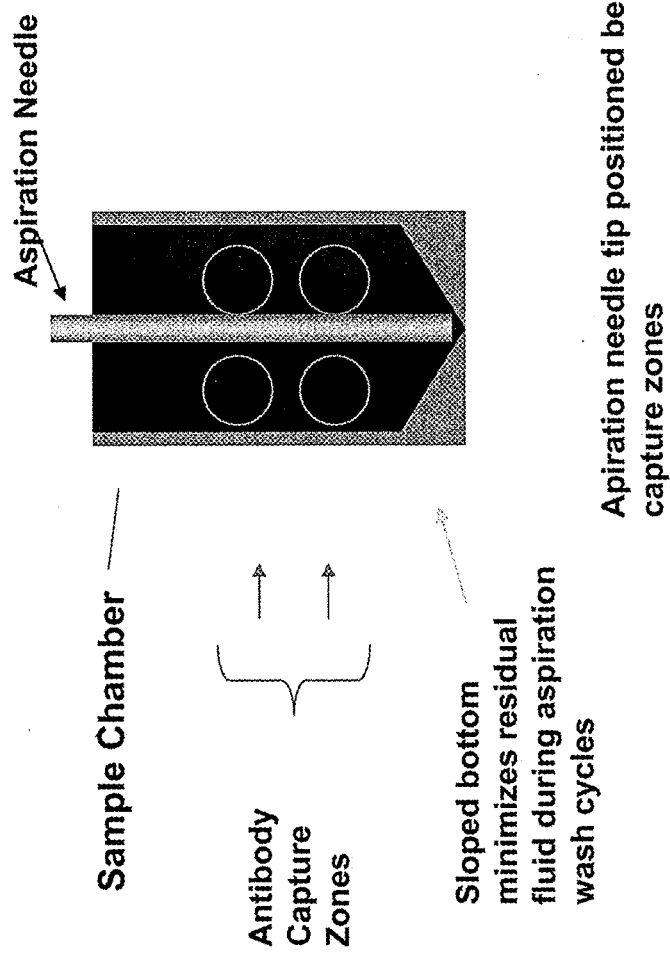
FIG. 8 shows reagent aspiration in an immunoassay cuvette.

FIG. 8 shows the insertion of the aspiration needle to the bottom of the immunoassay cuvette. With the capture zones on the vertical walls, removal of the fluid is achieved without locating the needle near the capture zones, consequently avoiding denaturation of binding regents by air flow. The bottom of the immunoassay cuvette is preferred to be sloped or curved. The sloping bottom with a cusp in the center/bottom of the device further enhances efficient fluid drainage and aspiration.

Figure 9:
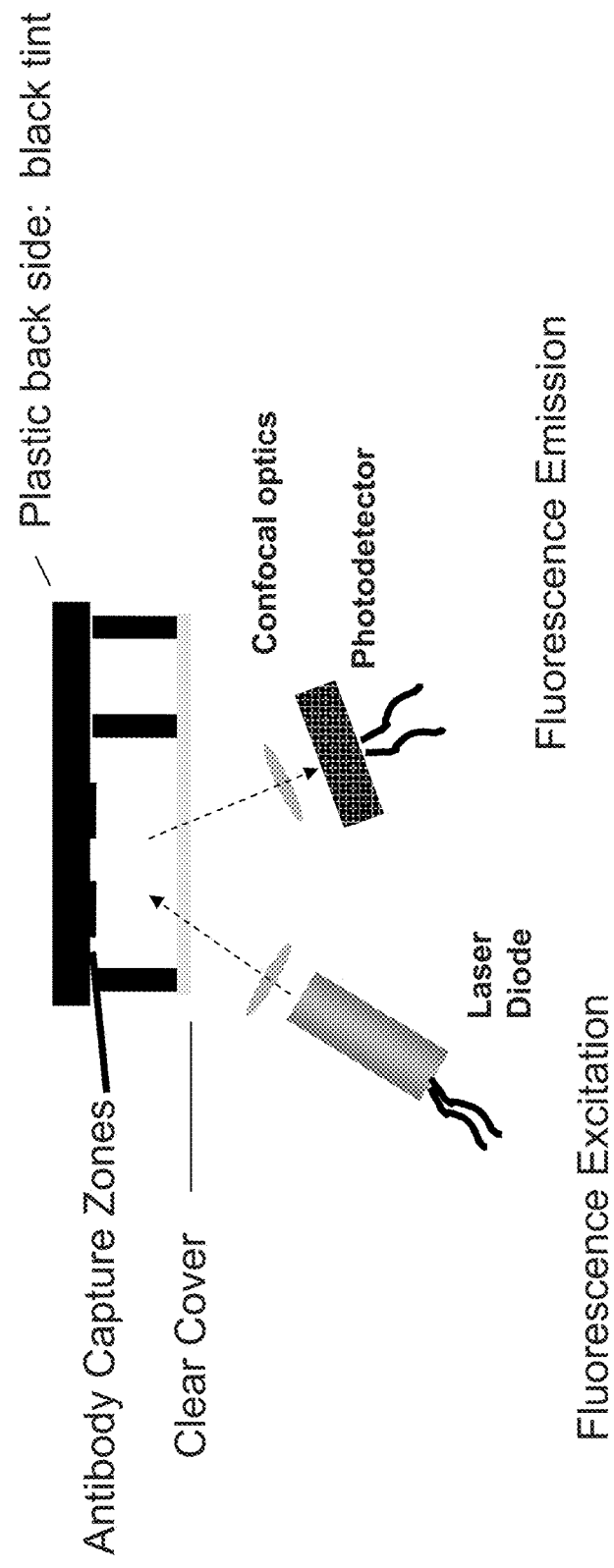
FIG. 9 shows the design of fluorescence detection in an immunoassay cuvette.

FIG. 9 diagrams one of the possible detection elements that can be used in conjunction with the immunoassay cuvette. Detection employing fluorescent dyes is one preferred detection method although there are other possible techniques such as chemiluminescence and enzyme activity. Assays are designed to incorporate the fluorescent dye into the binding complex formed in the capture zone when analyte is present. The back wall of the immunoassay cuvette that contains the antibody capture zones is comprised of a plastic material that is formulated with a tinting agent that reduces the background fluorescence of the plastic material. Although alternative low fluorescence substrates (glass and quartz) can be used, plastic is the most desirable since it can be molded at low cost with the appropriate dimensions, surface features, etc. Standard plastics as PMMA and polystyrene have relatively high levels of intrinsic fluorescence, which would be detected as background signal, thus they are limited in their application to high sensitivity fluorescence based solid phase immunoassays. The use of tinting agents can reduce their fluorescence. FIG. 9 shows the top view of the immunoassay cuvette and its orientation to the fluorescence detection subsystem comprising a laser diode for excitation and a photodetector to monitor fluorescence emission. The front wall opposing the antibody capture zones is made of a clear plastic material that allows for the fluorescence detection in the capture zones. The optics the detection system are designed to minimize any possible contribution of the clear plastic to the fluorescence measurement.

Two Chamber Immunoassay Cuvettes

In an alternative embodiment of the invention, the immunoassay cuvettes comprise two chambers: a sample reaction chamber and a signal reagent chamber, separated by a partition wall. The sample chamber comprises a first front wall, a first back wall, a first side wall, the partition wall, a first bottom, and a first top opening. The first back wall has substantially planar surface, which comprises a capture zone, where the capture reagents are non-diffusely bound, and optionally a binding reagent zone with the binding reagent diffusively bound to the non-porous wall of the sample chamber. The signal reagent chamber comprises a signal reagent zone, and optionally a binding reagent zone, where the signal reagents and binding reagents are diffusely bound to the non-porous surface of the wall in the signal reagent chamber.

Figure 10:
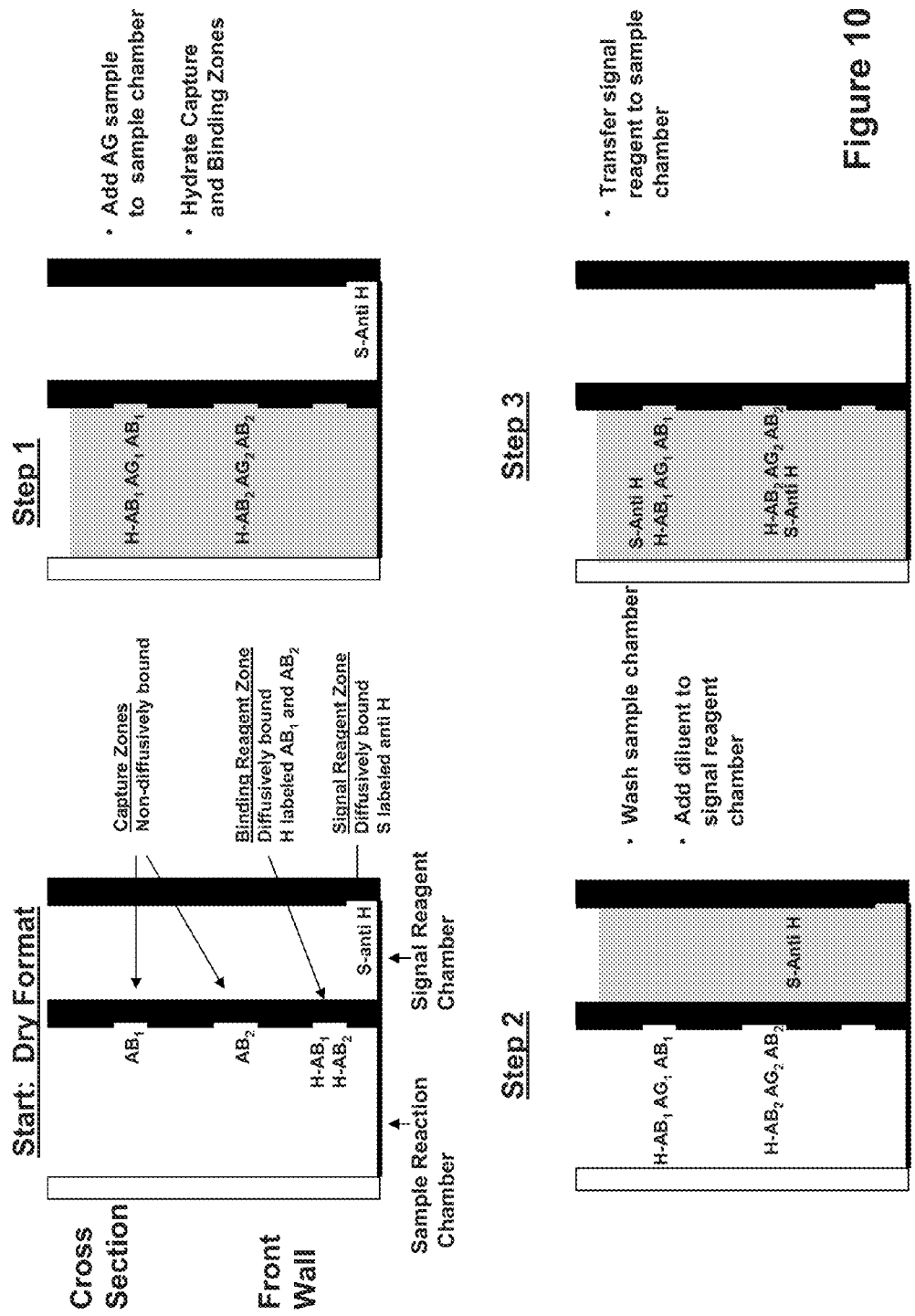
FIG. 10 shows an multiple analyte format in two chambers.

FIG. 10 depicts an assay format for multiple analyte detection in the same sample using the two chamber immunoassay cuvette. The sample contains two analytes where their respective antibodies are immobilized in separate capture zones on the back wall of the sample reaction chamber. The second antibodies of the sandwich pairs are deposited in the binding reagent zone. Both second antibodies are labeled with a hapten "H". The purpose of the hapten H is to link immune complexes formed in the captures zones with an anti-H reagent labeled with a fluorescent dye. The fluorescent anti-H is positioned in an adjacent signal reagent chamber of the device. Sample is added to the sample reaction chamber to start the assay. After a brief incubation period, the sample chamber is washed several times to remove unbound antibody. Diluent is added to the signal reagent chamber and an aliquot of the fluorescent label anti-H is transferred to the sample reaction chamber and allowed to incubate followed by a wash sequence. Any immune complex formed between the antigen, immobilized antibody in the capture zone and the antibody tagged with H will also have the fluorescent anti-H bound in that capture zone. The fluorescence detection subsystem can then scan the capture zones to measure fluorescence.

EXAMPLES

Materials

Human myoglobin, cat #1-023, Human troponin I, cat #1-020, and monoclonal antibodies for human roponin I, clones A34440 & G-129, and human myoglobin, clones 7005 & 7004, were obtained from Biospacific (Emeryville, Calif.). Polyclonal antibody to Human Ig (G & M), cat #109-005-044, and monoclonal antibody to fluorescein (F), cat #200-002-0370, were obtained from Jackson Immuno Research (West Grove, Pa.). The arylsulfonate cyanine dye, Cy5-NHS, cat #PA15101, was obtained from GE Healthcare, (Piscataway, N.J.). Hepatitis B core antigen (HBcAg), cat #YVS8914, and Hepatitis B surface antigen (HBsAg), cat #OBT 0912, were obtained form Accurate Chemical and Scientific Corp (Westbury, N.Y.). Fluorescein isothiocyanate (FITC), cat #F143, was from Invitrogen Corp. (Carlsbad, Calif.). Sucrose, BSA, phosphate buffered saline (PBS, pH 7.4), sodium carbonate, Tween 20, and sodium cholate were obtained from Sigma-Aldrich Corp. (St. Louis, Mo.). Fluorescence detection methodology is described in "Fluorescence Spectroscopy in Biology: Advanced Methods and their Application to Membranes, Proteins, DNA and Cells," vol. 3, ed. Wolfbeis, pub. Springer, 2005.

Example 1

Label Antibodies with Cy5

Anti-fluorescein, anti-troponin I (clone G-129), anti-myoglobin (clone 7004) and anti Ig (G&M) are labeled with Cy5-NHS as follows: To 1 mg. of antibody in 1 ml of 0.1M sodium carbonate buffer, pH 9.0, is added 40 ug of Cy5-NHS. The mixture is allowed to reacted for 3 hours at room temperature. The unconjugated Cy 5 is removed from the antibody by chromatography on a Sephadex G25 column. Spectral analysis indicates typically 2-4 Cy 5 molecules per antibody Anti-troponin I (clone G-129) and anti-myoglobin (clone 7004) are labeled with FITC as follows: To 1 mg of antibody in 1 ml of 0.1M sodium carbonate, pH 9.0, is added 30 ug of FITC. The mixture is allowed to react for 3 hours at room temperature, followed by chromatography on a Sephadex G25 column to remove unconjugated FITC. Spectral analysis indicates around 2 FITC molecules per antibody.

Example 2

One-Step Sandwich Assay, Antigen Samples

With the back wall in the horizontal position, 3 µl of anti-troponin I (clone A34440) at 3 µg/ml in PBS is dispended in spot 2 and 5 µl anti-myoglobin (clone 7005) at 5 µg/ml in PBS is dispensed in spot 3. Spots 2 & 3 are designated as the capture zone (non-diffusively bound) The back wall is then placed in a humidified chamber and the protein allowed to adsorb to the plastic for overnight at room temperature. The protein solution is then removed from spots 2 & 3 with a micropipette. A wash cycle is then performed by adding 3 µl of assay buffer comprised of PBS, 1 mg/ml BSA and 0.1% Tween 20 to each of the spots. After about 10 seconds the buffer is removed. The wash cycle is repeated 5 times. After the last wash cycle 3 µl of a PBS buffer containing 10% sucrose and 1 mg/ml BSA is placed in each of the spots. Following a 30 second incubation, the sucrose/PBS buffer is removed from the spots leaving a thin fluid film on the surface of the spots. A 3 µl aliquot containing Cy5-anti-troponin I (clone G-129) and Cy5-anti-myoglobin (clone 7004), both at a concentration in 1 µg/ml in PBS buffer with 10% sucrose, 1 mg/ml BSA, and 1% sodium cholate detergent is dispensed in spot 1. Spot 1 is designated the signal zone (diffusively bound). The back wall, still in the horizontal position, is then placed in a 37 C convection oven and allowed to dry of 1 hour. Epoxy is then placed along the rim to the back wall and the front wall is bounded to the back wall to assemble the unitized cuvette. The cuvette is stored desiccated until use.

To perform the sandwich assay, 5 µl of a sample containing human myoglobin and troponin is dispensed at the bottom of the cuvette with a micropipette. 45 µl of assay buffer is added, sufficient to immerse both capture and signal reagent zones (see FIG. 3). To facilitate mixing and diffusion of the signal reagent, 20 µl of the mixture is withdrawn and dispensed rapidly back into the consumable with a micropipette, repeating several times over about a 10 second period. The assay mixture then incubates for 20 minutes at room temperature, at which point the assay mixture is removed followed by 4 wash cycles with 70 µl of assay buffer at each cycle. After the last wash cycle, 70 µl of assay buffer is added to the cuvette and the Cy 5 fluorescence is detected in spots 2 & 3 to respectively measure troponin I and myoglobin in the sample.

Example 3

One-Step Competition Assay

Figure 11:
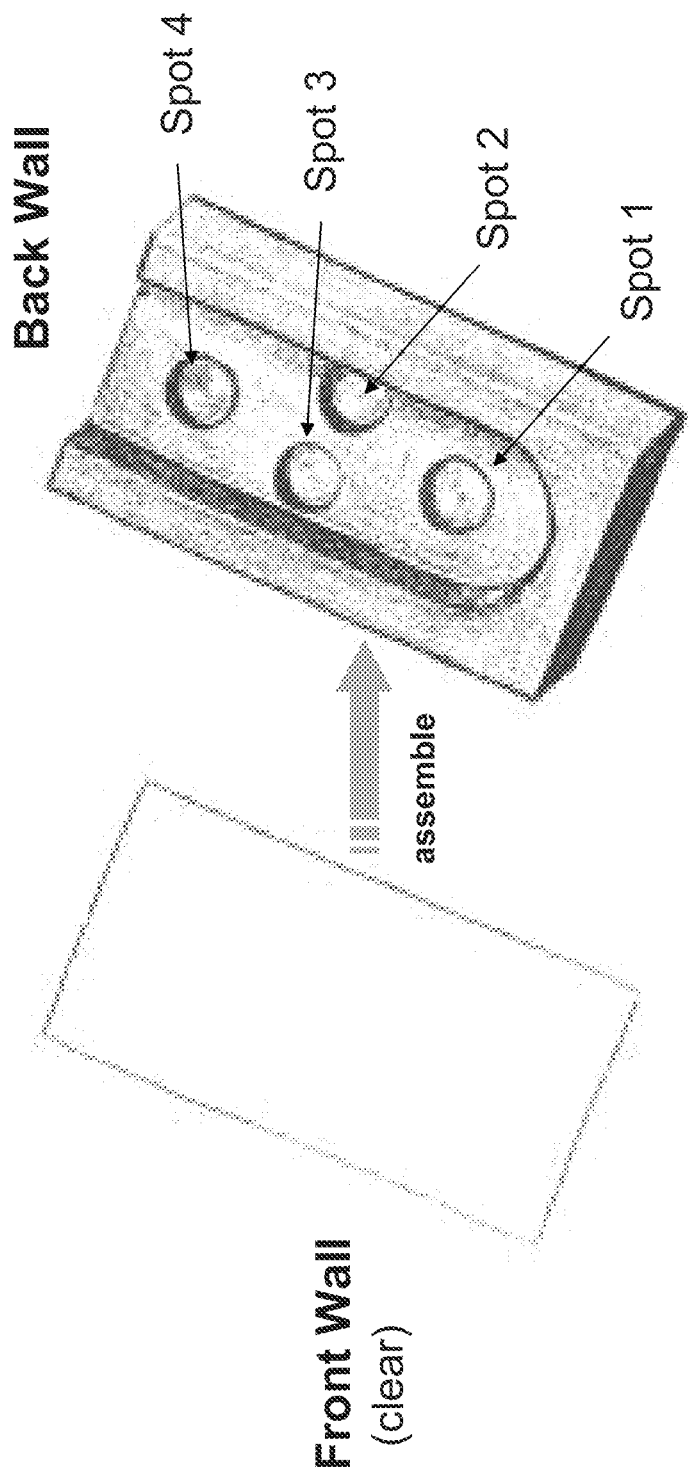
FIG. 11 shows the two-part assembly of an immunoassay cuvette.

FIG. 11 illustrates front and back walls of the unitized immunoassay cuvette prior to assembly. Both front and back walls are constructed with polymethmethyl acrylate plastic. The immunoassay cuvette has a height about 20-30 mm, a thickness about 1-10 mm (preferably 2-4 mm), and a width about 5-25 mm (preferably 5-15 mm). For example, the immunoassay cuvette is 25 mm high, 12 mm wide, and 5 mm thick with a liquid capacity of about 140 µl. For reagent formatting, the back wall is horizontally positioned. Using a micropipette, 3 µl of troponin I (0.5 ug/ml PBS) is placed in spot 2 and 3 µl of myoglobin (0.5 ug/ml in PBS) is placed in spot 3. Spots 2 & 3 are designated as the capture zone (non-diffusively bound) The back wall is then placed in a humidified chamber and the protein allowed to adsorb to the plastic for overnite at room temperature. The protein solution is then removed from spots 2 & 3 with a micropipette. A wash cycle is then performed by adding 3 µl of assay buffer comprised of PBS, 1 mg/ml BSA and 0.1% Tween 20 to each of the spots. After about 10 seconds the buffer is removed. The wash cycle is repeated 5 times. After the last wash cycle 5 µl of a PBS buffer containing 10% sucrose and 1 mg/ml BSA is placed in each of the spots. Following a 30 second incubation, the sucrose/PBS buffer is removed from the spots leaving a thin fluid film on the surface of the spots. 5 µl of a solution containing Cy5 anti-troponin I and Cy5-anti myoglobin, both at a concentration in 1 µg/ml in PBS buffer with 10% sucrose and 1% sodium cholate detergent. Spot 1 is designated the signal zone (diffusively bound). The back wall, still in the horizontal position, is placed in a 37 C convection oven and allowed to dry of 1 hour. Epoxy is then placed along the rim to the back wall and the front wall is bounded to the back wall to assemble the unitized cuvette. The cuvette is stored desiccated until use.

To perform the competitive assay, 5 µl of a sample containing human myoglobin and troponin is dispensed at the bottom of the cuvette with a micropipette. 45 µl of assay buffer is added, sufficient to immerse both capture and signal reagents zones, FIG. 4. To facilitate mixing and diffusion of the signal reagent, 20 µl of the mixture is withdrawn and dispensed rapidly back into the consumable with a micropipette, repeating several times over about a 10 second period. The assay mixture then incubates for 20 minutes at room temperature, at which point the assay mixture is removed followed by 4 wash cycles with 70 µl of assay buffer at each cycle. After the last wash cycle, 70 µl of assay buffer is added to the consumable and the Cy 5 fluorescence is detected in spots 2 & 3 to respectively measure troponin I and myoglobin in the sample.

Example 4

Two-Step Sequential Protocol with Amplification (Antigen Samples)

With the back wall in the horizontal position, 3 µl of anti-troponin I (clone A34440) at 5 ug/ml in PBS is dispended in spot 2 and 3 µl anti-myoglobin (clone 7005) at 5 ug/ml in PBS is dispensed in spot 3. Spots 2 & 3 are designated as the capture zone (non-diffusively bound) The back wall is then placed in a humidified chamber and the protein allowed to adsorb to the plastic for overnite at room temperature. The protein solution is then removed from spots 2 & 3 with a micropipette. A wash cycle is then performed by adding 3 µl of assay buffer comprised of PBS, 1 mg/ml BSA and 0.1% Tween 20 to each of the spots. After about 10 seconds the buffer is removed. The wash cycle is repeated 4 times. After the last wash cycle 3 µl of a PBS buffer containing 10% sucrose and 1 mg/ml BSA is placed in each of the spots. Following a 30 second incubation, the sucrose/PBS buffer is removed from the spots leaving a thin fluid film on the surface of the spots. A 3 µl aliquot containing F-anti-troponin I and F-anti-myoglobin, both at a concentration in 5 ug/ml in PBS buffer with 10% sucrose, 1 mg/ml BSA and 1% sodium cholate detergent is dispensed in spot 1. Spot 1 is designated the binding reagent zone (diffusively bound). A 3 µl aliquot of Cy5-anti F at 5 ug/ml in PBS with 10% sucrose, 1 mg/ml BSA, and 1% sodium cholate is dispensed in spot 4. Spot 4 is designated as the signal reagent zone. The back wall, still in the horizontal position, is then placed in a 37 C convection oven and allowed to dry of 1 hour. Epoxy is then placed along the rim to the back wall and the front wall is bounded to the back wall to assemble the unitized cuvette. The cuvette is stored desiccated until use.

To perform the sequential assay, 5 µl of a sample containing human myoglobin and troponin is dispensed at the bottom of the cuvette with a micropipette. 45 µl of assay buffer is added, sufficient to immerse both capture and binding reagent zones with the fluid remaining below the signal reagent zone. To facilitate mixing and diffusion of the binding reagent, 20 µl of the mixture is withdrawn and dispensed rapidly back into the consumable with a micropipette, repeating several times over a 10 second period. The assay mixture then incubates for 10 minutes at room temperature, at which point the assay mixture is removed followed by 4 wash cycles with 70 µl of assay buffer at each cycle, keeping the fluid level below the signal reagent zone. After the last wash cycle, 100 µl of assay buffer is added to the consumable, sufficient to immerse the signal reagent zone. To facilitate mixing and diffusion of the signal reagent, 20 µl of the mixture is withdrawn and dispensed rapidly back into the cuvette with a micropipette, repeating several times over a 10 second period. The assay mixture then incubates for 10 minutes at room temperature, at which point the mixture is removed followed by 4 wash cycles with 120 µl of assay buffer at each cycle. After the last wash cycle, 120 µl of assay buffer is added to the cuvette and the Cy 5 fluorescence is detected in spots 2 & 3 to respectively measure troponin I and myoglobin in the sample.

Example 5

Two-Step Sequential Protocol for Antibody Detection

With the back wall in the horizontal position, 3 µl of HBcAg at 1 ug/ml in PBS is dispensed in spot 2 and 3 µl of HBsAg at 1 ug/ml in PBS is dispensed in spot 3. Spots 2 & 3 are designated as the capture zone (non-diffusively bound). The back wall is then placed in a humidified chamber and the protein allowed to be adsorbed to the plastic for overnite at room temperature. The protein solution is then removed from spots 2 & 3 with a micropipette. A wash cycle is then performed by adding 3 µl of assay buffer comprised of PBS, 1 mg/ml BSA and 0.1% Tween 20 to each of the spots. After about 10 seconds the buffer is removed. The wash cycle is repeated 4 times. After the last wash cycle 3 µl of a PBS buffer containing 10% sucrose and 1 mg/ml BSA is placed in each of the spots. Following a 30 second incubation, the sucrose/PBS buffer is removed from the spots leaving a thin fluid film on the surface of the spots. A 3 µl aliquot of Cy5-anti Ig (G & M) at 5 ug/ml in PBS with 10% sucrose, 1 mg/ml BSA, and 1% sodium cholate is dispensed in spot 4. Spot 4 is designated as the signal reagent zone (diffusively bound). The back wall, still in the horizontal position, is then placed in a 37 C convection oven and allowed to dry of 1 hour. Epoxy is then placed along the rim to the back wall and the front wall is bounded to the back wall to assemble the unitized cuvette. The cuvette is stored desiccated until use.

To perform the sequential antibody assay, 5 µl of a sample containing anti HBcAg and anti HBsAg is dispensed at the bottom of the cuvette with a micropipette. 45 µl of assay buffer is added, sufficient to immerse the capture reagent zone with the fluid remaining below the signal reagent zone. To facilitate mixing, 20 µl of the mixture is withdrawn and dispensed rapidly back into the consumable with a micropipette, repeating several times over a 10 second period. The assay mixture then incubates for 10 minutes at room temperature, at which point the assay mixture is removed followed by 4 wash cycles with 70 µl of assay buffer at each cycle, keeping the fluid level below the signal reagent zone. After the last wash cycle, 100 µl of assay buffer is added to the consumable, sufficient to immerse the signal reagent zone. To facilitate mixing and diffusion of the signal reagent, 20 µl of the mixture is withdrawn and dispensed rapidly back into the cuvette with a micropipette, repeating several times over a 10 second period. The assay mixture then incubates for 10 minutes at room temperature, at which point the mixture is removed followed by 4 wash cycles with 120 µl of assay buffer at each cycle. After the last wash cycle, 120 µl of assay buffer is added to the cuvette and the Cy 5 fluorescence is detected in spots 2 & 3 to respectively measure anti HBcAg and anti HBsAg in the sample.

What is claimed is:

1. An immunoassay cuvette comprising a transparent front wall, a back wall, side walls, a bottom, and a top opening;
   the back wall has a substantially planar surface made of a non-porous material comprising a capture zone, and a first signal reagent zone;
   the capture zone comprises one or more spots non-diffusely bound with a defined antigen;
   the first signal reagent zone has one or more spots diffusely bound with a first signal reagent comprising an antibody against a human immunoglobulin;
   wherein the signal reagent zone is located above the capture zone.

2. The immunoassay cuvette according to claim 1, wherein the antibody is labeled with a signal generating molecule.

3. The immunoassay cuvette according to claim 2, wherein the signal generating molecule is a fluorescent dye, a chemiluminescent dye, or an enzyme.

4. The immunoassay cuvette according to claim 1, wherein the aspect ratio of the height to the width or the height to the thickness of the cuvette is at least 3 to 1.

5. The immunoassay cuvette according to claim 1, wherein the non-porous material is polymethmethacrylate, polystyrene, polycarbonate, glass, quartz, or combination thereof.

6. The immunoassay cuvette according to claim 1, wherein the back wall is black tinted.

7. The immunoassay cuvette according to claim 1, comprising a second signal reagent zone located above the first signal reagent zone, wherein the antibody in the first signal reagent zone is labeled with a first member of a binding pair, and the second signal zone comprises a conjugate of a signal generating molecule and a second member of the binding pair.

8. The immunoassay cuvette according to claim 7, wherein said binding pair consists of biotin and streptavidin.

9. The immunoassay cuvette according to claim 8, wherein the first member of the binding pair is biotin and the second member of the binding pair is streptavidin.

* * * * *